United States Patent [19]

Sauvage et al.

[11] Patent Number: 4,911,713
[45] Date of Patent: Mar. 27, 1990

[54] METHOD OF MAKING VASCULAR PROSTHESIS BY PERFUSION

[76] Inventors: Lester R. Sauvage, 1210 - 22nd East, Seattle, Wash. 98112; Svetlana Kaplan, 22603 - 66th Ave. West, Mountlake Terrace, Wash. 98043

[21] Appl. No.: 7,369

[22] Filed: Jan. 27, 1987

Related U.S. Application Data

[63] Continuation-in-part of Ser. No. 844,097, Mar. 26, 1986, abandoned.

[51] Int. Cl.⁴ .............................................. A61F 2/06
[52] U.S. Cl. .......................................... 623/1; 623/11; 623/66; 623/901; 8/94.11
[58] Field of Search ............ 8/94.11, 94.19 R, 94.33; 623/1, 2, 11, 66, 901; 128/334 R, DIG. 8

[56] References Cited

U.S. PATENT DOCUMENTS

| | | | |
|---|---|---|---|
| 3,106,483 | 10/1963 | Kline et al. | 623/1 |
| 3,438,374 | 4/1969 | Falb et al. | 128/334 R |
| 4,082,507 | 4/1978 | Sawyer | 623/66 |
| 4,083,066 | 4/1978 | Schmitz et al. | 623/1 |
| 4,108,161 | 8/1978 | Samuels et al. | 623/1 |
| 4,167,045 | 9/1979 | Sawyer | 623/2 |
| 4,358,470 | 11/1982 | Rasmussen | 8/94.11 |
| 4,372,743 | 2/1983 | Lane | 623/1 |
| 4,664,658 | 5/1987 | Sawada et al. | 128/334 R |

OTHER PUBLICATIONS

The American Heritage Dictionary, Second College Edition, 1982, p. 922.

*Primary Examiner*—Richard J. Apley
*Assistant Examiner*—Paul Prebilic
*Attorney, Agent, or Firm*—Seed and Berry

[57] ABSTRACT

A method of making an impermeable vascular prosthesis is disclosed which comprises the steps of treating a porous textile conduit with a first solution of cross-linking agent; perfusing the conduit with a second solution of cross-linking agent and protein; and drying the perfused conduit to allow gelation in a second solution to form an impermeable vascular prosthesis. Perfusion of the lumen of the prosthesis is performed with sufficient pressure to ensure that all interstices of the porous textile conduit are completely filled. A gelation mixture comprising albumin and glutaraldehyde is preferably utilized for perfusion of the prosthesis. Methods for preserving these grafts indefinitely by treatment with glycerol and other alkyl alcohols are also disclosed.

38 Claims, 1 Drawing Sheet

METHOD OF MAKING VASCULAR PROSTHESIS BY PERFUSION

RELATED APPLICATIONS

This application is a continuation-in-part of Ser. No. 844,097 filed March 26, 1986 now abandoned.

TECHNICAL FIELD

The present invention relates generally to the methods of making impermeable vascular prostheses, and more specifically, to improved methods of manufacture and preservation of albuminated knit polyester arterial grafts.

BACKGROUND ART

Advances in cardiovascular surgery during the past two decades have created a demand for artificial prostheses to replace and repair portions of the human vasculature which become damaged due to disease and injury. The ideal vascular prothesis should be impervious to blood loss even in the heparinized patient on cardiopulmonary bypass. The prothesis should also have good surgical handling characteristics, have low flow surface thrombogenicity (i.e., inability to activate platelets, white blood cells and factor XII), be free from embolic complications, have no adverse effect on blood, have at implantation or develop thereafter features that encourage outer wall healing by fibroblastic ingrowth from the perigraft tissues, and have intrinsic strength adequate for indefinite dimensional stability.

In addition, it would be desirable to provide a prosthesis which remains pliable and preserved in a relatively dry state for an extended period to enhance its convenience to the surgeon.

Prior art prostheses have attempted to fulfill these essential requirements by providing polyester knit grafts which have been subjected to preclotting by treatment with the patient's blood to provide a fibrin matrix to seal the interstices of the graft. This method is disadvantageous in that it requires additional time to be expended by the surgeon as well as utilization of a volume of the patient's blood.

Other prior art grafts include those that are pretreated with gelatin to reduce the implantation porosity and to obviate the necessity for preclotting. Guidoin et al. (*J. Biomedical Materials Research* 18, 1059–1072, 1984) suggest utilizing polyester prostheses fabricated from polyethylene terephthalate by treating them with cross-linked albumin. The method disclosed by Guidoin et al. teaches the immersion of the prosthetic graft into a cross-linking solution of albumin and glutaraldehyde. Jordan et al., *Surgery* 53:1, 45 (1963) disclose impregnating Dacron TM vascular grafts with gelatin. Humphries et al. *Surgery* 50:6, 947 (1961), collagen-impregnated Dacron TM arterial prostheses. In the dry state, all of these prior art grafts are hard and cannot bend.

These and other prior art prostheses having cross-linked protein fail to provide sufficent impermeability at the time of implantation. This is due to the fact that at least some of the interstices of the grafts are void or incompletely filled. Consequently, the surgeon is faced with implanting arterial grafts which have a tendency to leak, which results in undesirable blood loss.

BRIEF DESCRIPTION OF THE DRAWING

The FIGURE is a diagrammatic representation of the apparatus employed in the methodology of the preferred embodiment.

DISCLOSURE OF THE INVENTION

Figure 1:
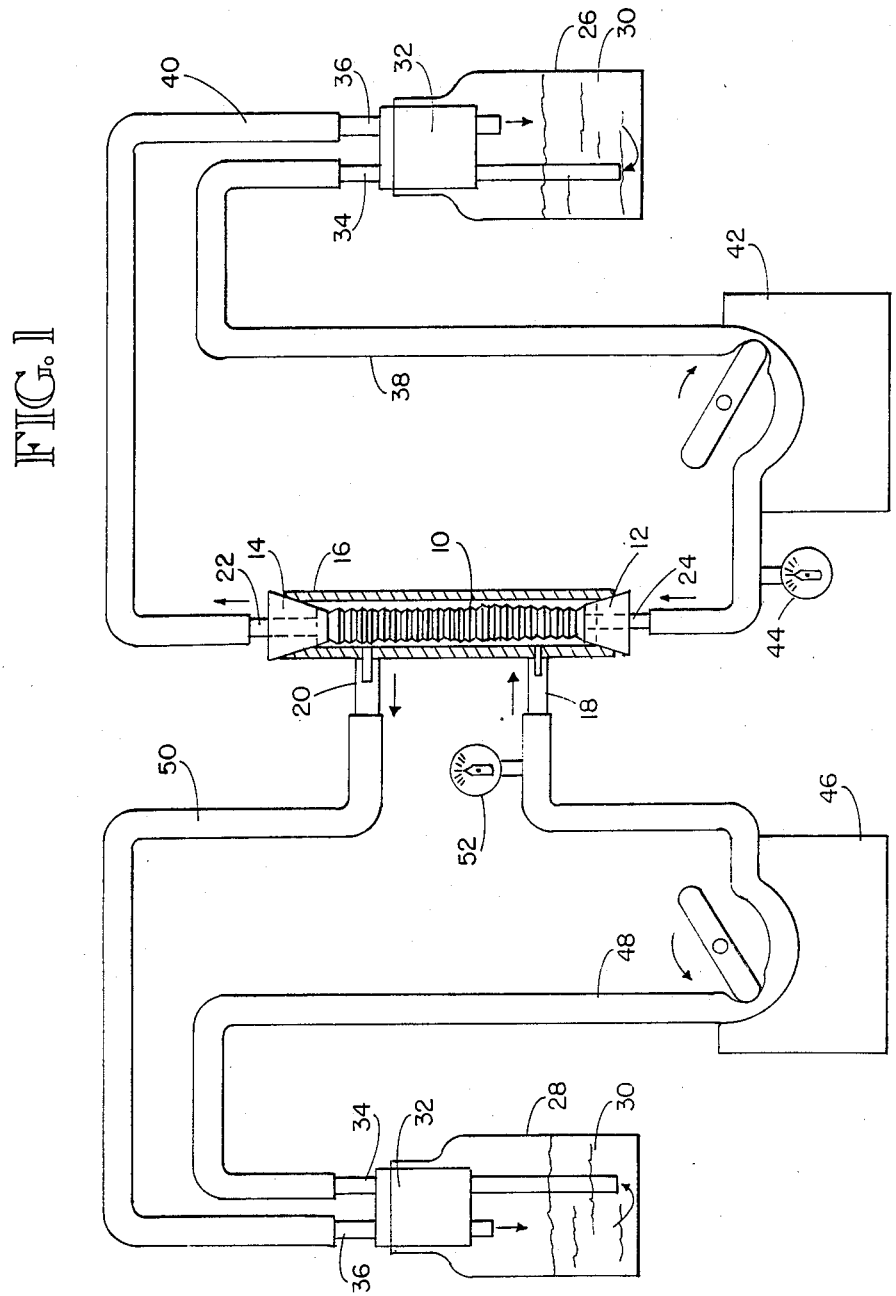

The present invention discloses improved methods for making an impermeable vascular prosthesis by ensuring that the interstices provided by woven and knit polyester grafts are sufficiently filled to ensure minimal blood loss at the time of implantation and to provide a stratum for enhanced tissue regeneration and healing of the vasculature.

The preferred method comprises first treating a porous textile conduit with a first solution of cross-linking agent. This conduit is subsequently perfused with a second solution of cross-linking agent and protein, and is then dried to allow gelation of the second solution to form an impermeable vascular prosthesis.

Treatment of the porous textile conduit is accomplished by perfusing the lumen of the conduit with the second solution with sufficient pressure to ensure that all pores or interstices of the porous textile conduit are completely filled. The preferable first solution is a solution of glutaraldehyde ranging in concentration from 0.3%–25% volume/volume (v/v). The second solution comprises a mixture of a solution of glutaraldehyde having a concentration ranging from 0.3%–25% (v/v) and a solution of albumin having a concentration ranging from 5%–50% weight/volume (w/v).

An alternative preferred embodiment of the methodology comprises the steps of perfusing the lumen of a porous textile conduit with a solution of cross-linking agent and protein, as defined above, and drying said perfused conduit to allow gelation of the solution to form an impermeable vascular prosthesis. In this method, the solution is perfused with sufficient pressure to ensure that all interstices of the porous textile conduit are completely filled. Optionally, the graft may be re-perfused and re-dried to ensure complete filling of the interstices of the graft.

Both preferred methodologies may optionally incorporate the additional step of perfusing the exterior of the conduit with a solution of cross-linking agent and protein. This method permits control of the pressure and pressure differential between the lumenal and exterior solutions to control the direction and rate of flow of said solutions through the pores of the conduit. Typically, the exterior and interior solutions have identical compositions but optionally may differ in composition.

An additional preferred embodiment provides a method for preserving a textile vascular prosthesis having cross-linked protein-filled interstices. This method comprises steps of treating the prosthesis with a solution of alkyl alcohol having at least two hydroxyl groups for a predetermined time and drying said prosthesis to produce a pliable, preserved prosthesis. Preferably prostheses made according to the methods disclosed herein can be preserved indefinitely by such method. Alternatively, any prosthesis having cross-linked protein-filled interstices may be advantageously preserved according to the methods disclosed herein. The preservation method preferably employs an alkyl alcohol selected from the group consisting of glycerol, ethylene glycol, propylene glycol, and trimethylene alcohol. The alkyl alcohol can be diluted with water, ethanol or methanol and can range in concentration from approximately 20% (v/v) to approximately 65% (v/v).

The preferred methodology for preserving such prosthesis may additionally comprise the step of pretreating the prosthesis with alcohol prior to the steps outlined above. This alcohol can be either ethanol or methanol and is preferably a 50% (v/v) aqueous solution of ethanol.

Another aspect of the present invention is an impermeable vascular prosthesis comprising a textile conduit having substantially all of its interstices filled with cross-linked protein and preserved by a solution of alcohol having at least two hydroxyl groups. In this embodiment, the preferred textile is knit or woven polyester, while the protein is selected from the group consisting of albumin, collagen and fibrinogen. The aldehyde cross-linking compound can be selected from the group consisting of glutaraldehyde, formaldehyde, acrolein and dialdehyde starches. The alkyl alcohol(s) employed for preservation purposes is preferably selected from the group consisting of glycerol, ethylene glycol, propylene glycol and trimethylene glycol.

Additionally, shelf-life of the grafts of the present invention can be extended by treatment with silicone.

BEST MODE FOR CARRYING OUT THE INVENTION

The principal advantage of the present invention lies in the fact that the method for producing vascular grafts disclosed herein results in substantially impermeable grafts at the time of implantation. The present methodology also obviates the necessity for preclotting of the graft utilizing the patient's blood. Finally, grafts produced according to the present methodology are impervious to blood loss even in heparinized patients on cardiopulmonary bypass. Moreover, these grafts have good surgical handling characteristics, have low flow surface thrombogenicity, are free from embolic complications, have minimal adverse effect upon blood, support outer wall healing by fibroblastic ingrowth from the perigraft tissues, and have intrinsic strength adequate for long-term dimensional stability.

Preferably, the grafts produced by the methods of the present invention remain pliable indefinitely and are conveniently preserved and sterilized for use by the surgeon.

Prior art methodologies for preparing prosthetic grafts include soaking knit and woven polyester conduits in a solution of glutaraldehyde and albumin. Glutaraldehyde is a well-known cross-linking agent for protein, such as albumin. Consequently, when glutaraldehyde is mixed with a solution of albumin, cross-linking occurs, which results in gelation of the albumin. When a freshly mixed solution of glutaraldehyde and albumin is applied to a knit polyester graft, the gelled albumin fills the interstices of the graft. Unfortunately, prior art methodologies are not adequate for complete filling of all interstices by soaking, which results in imperfect grafts. These grafts can create a substantial problem for the surgeon and the patient as blood loss is a serious, undesirable side effect in cardiovascular surgery.

Pretreatment of the graft with cross-linking agent according to the present invention provides that gelation time for the cross-linking agent and protein mixture can be controlled such that gelation of the mixture within the interstices of the graft occurs more rapidly than gelation at the surface of the graft. This differential control of gelation time results in greater impermeability of the graft compared to grafts prepared by prior art methods.

Moreover, pretreatment ensures that the protein subsequently added to the graft has sufficient cross-linking agent available within the interstices to ensure complete gelation and filling with the gelled protein. In order to ensure that the graft is impermeable, each interstice of the graft must be completely filled with fully gelled protein. Consequently, the pretreatment step with cross-linking agent enhances the likelihood of complete gelation within the interstices with concomitant increase in the graft's impermeability to blood.

While albumin is the preferred protein for cross-linking and glutaraldehyde is the preferred cross-linking agent, it is contemplated that other proteins, such as fibrinogen and collagen, may be substituted for albumin. Moreover, other cross-linking agents, such as acrolein, formaldehyde or dialdehyde starches, may be substituted for glutaraldehyde. It is essential that the cross-linking molecule possess at least one aldehyde moiety to adequately cross-link the protein. It is contemplated that homogeneous mixtures of proteins, such as albumin and collagen, fibrinogen and collagen, and albumin and fibrinogen, may be also useful in the preparation of these grafts.

The present methodology provides a convenient means for adjusting the gelation time of the protein/cross-linking mixture. The gelation time of a glutaraldehyde-albumin solution is approximately inversely proportional to the concentration of glutaraldehyde in the glutaraldehyde-albumin solution. Thus, increasing the concentration of glutaraldehyde decreases the gelation time.

In the preferred embodiment, it is desirable to pretreat the graft with a first solution of 10% (v/v) glutaraldehyde. This first solution of glutaraldehyde can range in concentration from 0.3%–25% (v/v). A preferred second solution for the subsequent perfusion of the graft comprises a glutaraldehyde-albumin solution in equal parts of a 0.95% (v/v) glutaraldehyde solution and a 25% (w/v) albumin solution. Alternatively, the final concentration of the glutaraldehyde solution can range from 0.4%–1.0% (v/v) and the final concentration of the albumin solution can range from 6%–15% (w/v).

Utilizing the concentrations of the preferred second solution, it has been found that the gelation time of the second solution can be controlled (1) by varying the concentration of the glutaraldehyde in the first solution and (2) by varying the total volume of the second solution for perfusing the graft after initial treatment with the first solution. For example, where a 10% (v/v) glutaraldehyde solution is used to pretreat a graft and the volume of this solution retained by the graft after pretreatment equals approximately 0.5% (v/v) of the total volume of the second solution to be perfused through the graft, a gelation time of approximately 15 minutes is achieved. By comparison, when the 10% (v/v) glutaraldehyde solution is again utilized but the graft retains a 1% (v/v) fraction of the second solution of glutaraldehyde and albumin, the gelation time is reduced from approximately 15 minutes to 10 minutes. Where the first solution is 7% (v/v) of glutaraldehyde and the graft retains 0.5% (v/v) of the volume of the subsequently perfused glutaraldehyde-albumin solution, the gelation time is approximately 20 minutes. Thus, one can conveniently select the gelation time by either adjusting the initial concentration of the glutaraldehyde solution in which the graft is first treated and/or adjusting the total volume of the second solution.

In practice, the amount of the first solution retained by the graft is determined by comparing the dry weight prior to treatment with the wet weight of the graft after treatment with the glutaraldehyde solution. The preferred first solution has a density of approximately 1 gm/ml.

The preferred methodology of the present invention employs a knit Dacron ™ graft, such as Bionit I ®, Bionit II ® or Bionit II ® EXS (Bard Implants Division, Billerica, Massachusetts). The length and diameter of the graft are selected by the surgeon. The selected graft is first treated by perfusing in a solution of cross-linking agent. The graft is then perfused with a solution of cross-linking agent and protein in the apparatus shown in the figure.

A section of porous knit polyester graft 10 forms a conduit having one end frictionally coupled to the exterior of a conical first stopper 12 and the other end similarly coupled to a conical second stopper 14. Said stoppers are disposed within the ends of a glass or plastic tube 16 and are adapted to seal the ends of the tube. The tube defines an inlet 18 and an outlet 20. The stoppers 12 and 14 define passageways for receiving an inlet fitting 24 and an outlet fitting 22. First and second reservoirs 26 and 28, respectively, each contain a volume of solution 30 for perfusing the graft 10. The openings of the reservoirs are adapted to receive stoppers 32, each adapted to receive an outlet coupling 34 and an inlet coupling 36. The outlet 34 of the first reservoir 26 is coupled to the inlet fitting 24 of the first stopper 12 by means of a rubber or plastic tubing 38. The inlet 36 of the first reservoir 26 is similarly coupled to the outlet fitting 22 of the second stopper 14 by means of a plastic or rubber tube 40. A first peristalic pump 42 engages the tubing 38 for selectively pumping fluid 30 from the first reservoir 26 through the outlet 34 into the inlet 24 at the first stopper 12. Said fluid is then caused to flow through the lumen of the graft 10 and exit through the outlet 22 of the second stopper 14 and through the tubing 40 into the first reservoir 26 through its inlet 36. A first pressure gauge 44 monitors the output pressure of the first peristaltic pump 42.

A second peristaltic pump 46 engages a plastic or rubber tube 48, which couples the outlet 34 of the second reservoir 28 to the inlet 18 of the tube 16. Fluid 30 contained within the second reservoir 28 is pumped by a second peristaltic pump 46, enters the tube 16 through its inlet 18, and is caused to flow over the exterior of the graft 10 and exit through the outlet 20 of the tube 16, which is coupled to the inlet 36 of the second reservoir 28 through a rubber or plastic tube 50. A second pressure gauge 52 monitors the output pressure of the second peristaltic pump 46.

The apparatus of the present method conveniently allows the lumen of the graft to be perfused with a solution of protein and cross-linking agent with sufficient pressure to cause flow through the interstices of the graft from the lumen to the exterior of the graft, thus ensuring that all of the interstices of the porous textile conduit are completely filled. Perfusion of the exterior of the graft can also be accomplished by the apparatus. This exterior perfusion is preferably initiated at some time after the initiation of the perfusion of the lumen of the graft.

After the tube containing the graft is completely filled, the pressure of the lumenal perfusion and the pressure of the exterior perfusion can be adjusted. Additionally, the patency of a graft may be tested after gelation is completed. If a pressure differential between the solution perfusing the lumen of the graft and that externally perfusing the prepared graft cannot be maintained, such condition indicates that the graft leaks and thus is not acceptable.

Preservation of the aforementioned grafts as well as other textile vascular prostheses having cross-linked protein filled interstices provides substantial advantages for the surgeon. For instance, preservation of these grafts in the "dry" state reduces the likelihood of contamination. Alternatively, grafts preserved in a dry state can be sterilized at the point of manufacture and shipped in containers designed to ensure sterility over extended periods of time. Acceptable sterilization techniques include use of gamma irradiation and cold gas ethylene oxide.

Those grafts preserved according to the present invention remain pliable and facilitate implantation. Prior art protheses must be shipped and stored in a wet state, which renders them susceptible to contamination and leakage. By contrast, prior art protheses are dried to a hard, brittle state and then rehydrated prior to surgery. This is inconvenient and requires additional time to be expended by the surgeon.

The present invention teaches a novel method of preserving vascular protheses, comprising a flexible textile conduit, having its interstices filled with cross-linked protein. These grafts are transferred to a 50% (v/v) ethanol solution for a period ranging from 3 to 24 hours. The grafts are then allowed to air-dry for several hours and then are immersed in a glycerol solution for at least two hours and preferably ranging from two to ten hours. The glycerol solution is preferably a 50% (v/v) aqueous solution of ethanol and can range from 20% to 65% (v/v). Alternatively, glycerol may be provided in a 50% aqueous solution to be diluted to a final concentration of 20%-65% (v/v) glycerol. After the treated grafts are removed from the glycerol solution, they are allowed to air-dry for five to six hours and then are appropriately sterilized and packaged. It has been found that glycerol and other alkyl alcohols provide ideal means for preserving cross-linked protein prosthesis. For example, ethylene glycol, propylene glycol and trimethylene glycol can be substituted for glycerol in this process.

An additional and optional feature of the present invention includes the method for enhancing the shelf-life of the grafts produced to the aforementioned methodologies. Specifically, such grafts are coated with a thin film of silicone to limit dehydration. The grafts are immersed in a solution of silicone or silicone derivative dissolved in a volatile solvent selected from the group consisting of ether, toluene and hexane. The silicone can be silicone gel, oil or other commonly available forms of silicone. The preferred concentration of silicone is 5% (w/w) but can range from 1% to 50%. The silicone-treated grafts are then removed from the silicone solution and allowed to air-dry, resulting in evaporation of the solvent and deposition of a thin layer of silicone on the intimal and exterior surfaces of the grafts. Alternatively the silicone solution can be applied to the grafts by spraying.

In the examples that follow, Example I discloses a first preferred methodology of producing albuminated, impermeable vascular grafts incorporating the step of pretreatment with a solution of cross-linking agent. Example II is for an alternative preferred embodiment of the methodology wherein the pretreatment step is not utilized, but perfusion of the lumen of the graft is done with sufficient pressure to ensure filling of all interstices. This example also discloses the additional steps of re-perfusion and re-drying after the first perfusion and drying. These additional steps ensure complete filling. Example III sets forth test protocol and data for comparing the efficacy of grafts made according to the methodology of the present invention with those made according to prior art methods. Examples IV and V disclose the methodology for preserving the grafts produced by the methods of Example I.

EXAMPLE I

A length of 30 cm of Bionit II ® Dacron TM graft was selected, weighed and then perfused for 1 hour in a 10% (v/v) aqueous glutaraldehyde solution. After the graft was so treated, excess glutaraldehyde solution was removed by squeezing the graft gently. The graft was then weighed to determine the increase in the weight of the glutaraldehyde-treated graft over the dry graft (2.35 gm) and was determined to be 0.5% (w/v) of the total volume of the glutaraldehyde-albumin mixture subsequently utilized in perfusing the graft.

The glutaraldehyde-treated graft was attached to the apparatus shown in the figure. 235 ml of glutaraldehyde-albumin mixture was added to the first reservoir and 235 ml to the second reservoir. These solutions were identical in composition and comprised equal volumes of 0.95% (v/v) glutaraldehyde in water and 25% (w/v) human albumin in saline. The human albumin is commercially available from the New York Blood Center, Inc., New York, New York.

The solution contained in the first reservoir was perfused by means of the first perfusion pump through the lumen of the graft for 2 minutes at a low pressure (less than 40 mm Hg) above atmospheric pressure. The glutaraldehyde-albumin solution passed through the pores of the graft, partially filling the void between the exterior of the graft and the interior of the tube. The exterior of the graft was then perfused with the glutaraldehyde-albumin solution by means of the second peristaltic pump. After the system was completely filled, the pressure of the interior solution was adjusted to 60 mm Hg above atmospheric pressure. Because the interstices of the graft were not filled with gelled albumin, the pressure was equilibrated between the lumen of the graft and the exterior of the graft due to outward flow through the interstices. Perfusion was maintained for 11 minutes. During the last few minutes, pressure differential was achieved between the lumen and the exterior of the graft. The graft was removed, emptied, slightly stretched, and longitudinally rotated slowly with air perfusion for 20 minutes to cause uniform gelation of the albumin. The graft was then air-dried for 1 hour. The graft so produced was stored in a saline solution until used.

EXAMPLE II

A length of Bionit II ® Dacron TM graft selected by the surgeon was attached to the apparatus shown in the figure. 150 ml of glutaraldehyde-albumin mixture was added to the first reservoir and 150 ml to the second reservoir. This solution comprised equal volumes of 0.95% (v/v) glutaraldehyde in water and 25% (w/v) albumin in saline.

The solution contained in the first reservoir was perfused by means of the first perfusion pump through the lumen of the graft for 2 minutes at low pressure (less than 40 mm Hg above atmospheric pressure. The glutaraldehyde-albumin solution passed through the pores of the graft, partially filling the void between the exterior of the graft and the interior of the tube. The exterior of the graft was then perfused with the glutaraldehyde-albumin solution by means of a second peristaltic pump. After the system was completely filled, the pressure of the interior solution was adjusted to 60 mm Hg above atmospheric pressure. Because the interstices of the graft were not filled with gelled albumin, the pressure was equilibrated between the lumen of the graft and the exterior of the graft due to flow through the interstices. Perfusion was maintained for 25 minutes whereupon the graft was removed, emptied, slightly stretched, and longitudinally rotated slowly with an air perfusion for 20 minutes to cause uniform gelation of the albumin. The graft was then air-dried for 1 hour.

The graft was then reinstalled in the apparatus shown in the figure, and the graft was re-perfused and re-dried in the identical manner. The graft so produced was stored in saline solution until used.

EXAMPLE III

To determine the efficacy of the grafts of the present invention with respect to blood loss, a series of in vivo experiments were conducted. Implantations were conducted utilizing the grafts of the present invention as well as prior art grafts.

Mongrel dogs were used in each test. The subjects were cared for according to the standards of the American Association for Accreditation of Laboratory Animal Care. All dogs were healthy both pre- and postoperatively, and of comparable weight (15 to 25 kg) for the different series. They were anesthetized with thiamylal sodium (Bio-tal) and maintained on a mixture of 0.5–1.0% halothane (Fluothane) with room air.

Bionit ® warp-knit external-velour Dacron TM prostheses 6 cm long and 8 cm in diameter were used to restore continuity of the descending thoracic aorta in systemically heparinized canines (3 mg/kg) after a 5 cm segment of the thoracic aorta had been excised. Anastomotic bleeding was prevented by wrap of Teflon ® felt. Transinterstice blood loss was measured by differential weighing of the sponges which had absorbed it.

The data in Table 1 show the results of this comparative experiment.

TABLE 1

| Prior Art Grafts | | Grafts Produced by the Present Invention | |
|---|---|---|---|
| Case | Blood Losss (ml) | Case | Blood Loss (ml) |
| T608 | 72 | V295 | 0 |
| T622 | 65 | V304 | 0 |
| T623 | 30 | V305 | 0 |
| T624 | 45 | V311 | 0 |
| T631 | 18 | V322 | 0 |
| T634 | 30 | V324 | 3 |
| T621 | 100 | V325 | 3 |
| T638 | 71 | V327 | 0 |
| T651 | 49 | V332 | 5 |
| T653 | 34 | V333 | 5 |
| T657 | 20 | V336 | 0 |
| T659 | 20 | V345 | 2 |
| T671 | 10 | | |
| T699 | 66 | | |

TABLE 1-continued

| | Prior Art Grafts | Grafts Produced by the Present Invention | |
|---|---|---|---|
| Case | Blood Losss (ml) | Case | Blood Loss (ml) |
| Average = | 45 | Average = | 1.5 |

The test data were generated from grafts prepared essentially according to the method as set forth in Example I. The control data were generated utilizing prior art grafts. In those experiments, grafts were prepared by soaking the grafts in a mixture of albumin and glutaraldehyde.

The data show that there was approximately a 30-fold difference in blood loss between the prior art methodology and those grafts prepared according to the methodology of the present invention. These data indicate that blood loss through the interstices of the graft is substantially reduced by utilizing grafts that are prepared according to the method disclosed herein.

EXAMPLE IV

The grafts produced in Example I were transferred to a 50% (v/v) aqueous solution of ethyl alcohol for a period of 12 hours. These grafts were then removed and allowed to air-dry for two hours. Following drying, the grafts were then transferred to a 50% (v/v) aqueous solution of glycerol for 2 hours. They were then removed and allowed to dry for 5 hours.

The grafts produced according to this example were sterilized utilizing gamma irradiation. They were subsequently stored in dry form in plastic containers. It was found that grafts prepared in accordance with this example remained pliable and easy to manipulate by the surgeon for a period exceeding 100 days.

EXAMPLE V

Grafts produced by the method of Example I were preserved in accordance with Example IV. These grafts were then immersed in a 5% (w/w) solution of silicon (Dow-Corning Silastic Medical Adhesive Silicone Type A) in toluene. The grafts were then removed from the silicone solution and the toluene was allowed to evaporate, resulting in a thin film of silicone being deposited on the surfaces of the graft.

From the foregoing, it will be appreciated that although specific embodiments of the invention have been described herein for purposes of illustration, various modifications may be made without deviating from the spirit and scope of the invention. For example, perfusion apparatus differing substantially from the structure shown in the figure may be utilized so long as similar results are achieved. Moreover, various combinations of cross-linking agents and protein may be utilized in the methodology of the present invention. For instance, the graft may be first treated with a combination of albumin and glutaraldehyde and dried. Subsequent treatment may include re-perfusing the lumen or exterior of the graft with a different combination of protein and cross-linking agent, thus producing a heterogeneous graft to provide differing strata for endothelial growth within the lumen and on the exterior of the graft. The methodology of the present invention permits a wide variety of combinations of proteins to be employed. Additionally, it may be desirable to perfuse the graft with homogeneous mixtures of proteins for various experimental and therapeutic purposes. Perfusates can also include growth-promoting factors, healing factors, antibiotics, and antithrombogenic agents or anticoagulants where therapeutically and/or physiologically desirable.

We claim:

1. A method of making an impermeable vascular prosthesis comprising the steps of:
   perfusing the interior of a textile conduit at a pressure and under conditions sufficient to fill substantially all of the interstices of said conduit with a first solution of cross-linking agent and protein;
   perfusing the exterior of the conduit with a second solution of cross-linking agent and protein;
   controlling the pressure and pressure differential between the first and second solutions to control the direction and rate of flow of said solutions through the interstices of said conduit; and
   drying said perfused conduit to allow gelation of the solution to form an impermeable vascular prosthesis.

2. The method of claim 1 wherein the second solution is perfused simultaneously with the first solution or is perfused after a predetermined interval.

3. The method of claim 1 wherein the compositions of the first and second solutions are identical.

4. The method of claim 1 wherein the cross-linking agent is characterized as having an aldehyde moiety.

5. The method of claim 1 wherein the cross-linking agent is selected from the group consisting of glutaraldehyde, formaldehyde, acrolein and dialdehyde starches.

6. The method of claim 1 wherein the cross-linking agent is a solution of glutaraldehyde.

7. The method of claim 1 wherein the cross-linking agent is a solution of glutaraldehyde ranging in concentration from 0.3%–25% (v/v).

8. The method of claim 1 wherein the protein is selected from the group consisting of albumin, collagen, and fibrinogen.

9. The method of claim 1 wherein the solution of cross-linking agent and protein comprises:
   glutaraldehyde having a final concentration ranging from 0.4%–1.0% (v/v); and
   albumin having a final concentration ranging from 6%–15% (w/v).

10. The method of claim 1 wherein the textile conduit is polyester.

11. The method of claim 10 wherein the textile conduit is polyethylene terephthalate.

12. The method of claim 1 wherein the step of drying the prosthesis comprises rotating the prosthesis about its longitudinal axis.

13. A method of making an impermeable vascular prosthesis comprising the steps of:
   perfusing the interior of a textile conduit with a first solution of cross-linking agent and protein;
   perfusing the exterior of the conduit with a second solution of cross-linking agent and protein;
   controlling the pressure and pressure differential between the first and second solutions to control the direction and rate of flow of said solutions through the interstices of said conduit;
   drying said perfused conduit;
   re-perfusing the interior of the conduit at a pressure sufficient to fill substantially all of the interstices of said conduit and under conditions sufficient to control the kinetics of gel formation; and
   re-drying said re-perfused conduit to form an impermeable vascular prosthesis.

14. The method of claim 13 wherein the second solution is perfused simultaneously with the first solution or is perfused after a predetermined interval.

15. The method of claim 13 wherein the compositions of the first and second solutions are identical.

16. The method of claim 13 wherein the cross-linking agent is characterized as having an aldehyde moiety.

17. The method of claim 13 wherein the cross-linking agent is selected from the group consisting of glutaraldehyde, formaldehyde, acrolein, and dialdehyde starches.

18. The method of claim 13 wherein the cross-linking agent is a solution of glutaraldehyde.

19. The method of claim 13 wherein the cross-linking agent is a solution of glutaraldehyde ranging in concentration from 0.3%–25% (v/v).

20. The method of claim 13 wherein the protein is selected from the group consisting of albumin, collagen, and fibrinogen.

21. The method of claim 13 wherein the solution of cross-linking agent and protein comprises:
   glutaraldehyde having a final concentration ranging from 0.4%–1.0% (v/v); and
   albumin having a final concentration ranging from 6%–15% (w/v).

22. The method of claim 13 wherein the textile conduit is polyester.

23. The method of claim 13 wherein the textile conduit is polyethylene terephthalate.

24. The method of claim 13 wherein the steps of drying and re-drying the prosthesis comprises rotating the prosthesis about its longitudinal axis.

25. A method of making an impermeable vascular prosthesis comprising the steps of:
   treating a porous textile conduit with a first solution of a cross-linking agent;
   perfusing said conduit with a second solution of cross-linking agent and protein;
   perfusing the exterior of the conduit with a third solution of cross-linking agent and protein;
   controlling the pressure and pressure differential between the second and third solutions to control the direction and rate of flow of said solutions through the interstices of said conduit; and
   drying said perfused conduit to allow complete gelation of the second solution to form an impermeable vascular prosthesis.

26. The method of claim 25 wherein the step of treating the porous textile conduit comprises the step of perfusing the interior of the conduit with the second solution with sufficient pressure to ensure that all interstices of the porous textile conduit are completely filled.

27. The method of claim 25 wherein the third solution is perfused simultaneously with the second solution or is perfused after a predetermined interval.

28. The method of claim 25 wherein the compositions of the second and third solutions are identical.

29. The method of claim 25 wherein the cross-linking agent is characterized as having an aldehyde moiety.

30. The method of claim 25 wherein the cross-linking agent is selected from the group consisting of glutaraldehyde, formaldehyde, acrolein, and dialdehyde starches.

31. The method of claim 25 wherein the cross-linking agent is a solution of glutaraldehyde.

32. The method of claim 25 wherein the cross-linking agent is a solution of glutaraldehyde ranging in concentration from 0.3%–25% (v/v).

33. The method of claim 25 wherein the protein is selected from the group consisting of albumin, collagen and fibrinogen.

34. The method of claim 25 wherein the second solution of cross-linking agent and protein comprises:
   glutaraldehyde having a final concentration ranging from 0.4%–1.0% (v/v); and
   albumin having a final concentration ranging from 6%–15% (w/v).

35. The method of claim 25 wherein the textile conduit is knit or woven.

36. The method of claim 35 wherein the textile conduit is polyester.

37. The method of claim 36 wherein the textile conduit is polyethylene terephthalate.

38. The method of claim 25 wherein the step of drying the prosthesis comprises rotating the prosthesis about its longitudinal axis.

* * * * *